US008276582B2

(12) United States Patent
Bridges et al.

(10) Patent No.: US 8,276,582 B2
(45) Date of Patent: Oct. 2, 2012

(54) RESPIRATOR ASSEMBLY

(75) Inventors: Peter Clive Bridges, Farnborough (GB); Adrian Huggins, Farnborough (GB); Barry Short, Fleet (GB)

(73) Assignee: Qinetiq Limited (GB)

( * ) Notice: Subject to any disclaimer, the term of this patent is extended or adjusted under 35 U.S.C. 154(b) by 2090 days.

(21) Appl. No.: 10/511,766

(22) PCT Filed: Apr. 25, 2003

(86) PCT No.: PCT/GB03/01776

§ 371 (c)(1), (2), (4) Date: Oct. 19, 2004

(87) PCT Pub. No.: WO03/095031

PCT Pub. Date: Nov. 20, 2003

(65) Prior Publication Data

US 2005/0115567 A1 Jun. 2, 2005

(30) Foreign Application Priority Data

May 8, 2002 (GB) .................................. 0210417.2

(51) Int. Cl.
*A62B 17/00* (2006.01)
*A61F 9/08* (2006.01)

(52) U.S. Cl. ......... 128/201.24; 128/200.28; 128/201.22; 128/201.23

(58) Field of Classification Search ............. 128/201.24, 128/200.28, 201.22, 201.23, 201.29, 202.11, 128/202.19, 202.27, 206.23, 206.24, 206.26, 128/206.21, 206.28; 2/8.2, 806
See application file for complete search history.

(56) References Cited

U.S. PATENT DOCUMENTS 2,642,574 A 6/1953 Eloranta
2,861,568 A * 11/1958 Quilter et al. ............ 128/201.23
2,935,985 A * 5/1960 Andrews et al. ......... 128/201.23
3,149,632 A * 9/1964 Colley ..................... 128/201.23
(Continued)

FOREIGN PATENT DOCUMENTS

DE 671117 2/1993
(Continued)

OTHER PUBLICATIONS

Webster's New World Dictionary, Third College Edition, 1988, p. 557, definition of gasket.*

(Continued)

*Primary Examiner* — Justine Yu
*Assistant Examiner* — Clinton T Ostrup
(74) *Attorney, Agent, or Firm* — McDonnell Boehnen Hulbert & Berghoff LLP

(57) ABSTRACT

A respirator assembly e.g. for NBC protection is formed from two separate sub-assemblies. The first sub-assembly comprises a flexible hood (or other suitable headgear), a rigid mounting ring and a peripheral face seal. The second sub-assembly comprise a face plate with lens, oronasal mask and inlet and outlet valves, and is demountably attachable to the ring. The first sub-assembly can be worn on its own with the user breathing ambient air through the front end, the second sub-assembly being added if and when a hazard is encountered. The positioning of the face seal in the first sub-assembly means that a comfortable and reliable fit can be ensured when the sub-assembly is donned prior to a mission, but the user is relieved of the physiological burden of wearing the complete respirator unless and until protection is required.

7 Claims, 3 Drawing Sheets

U.S. PATENT DOCUMENTS

Figure 1:
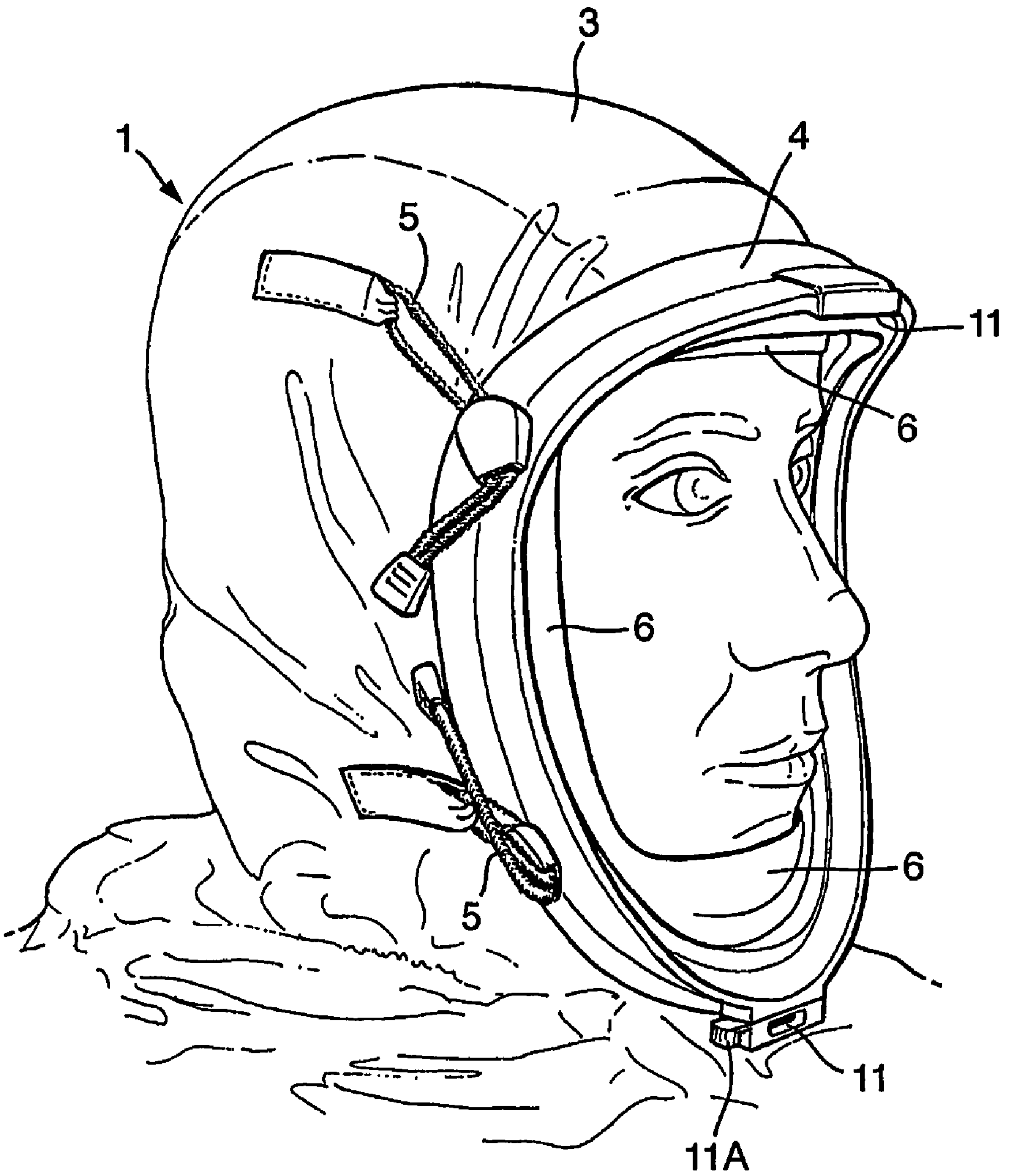

| | | | | | |
|---|---|---|---|---|---|
| 3,220,408 | A | * | 11/1965 | Silverberg | 128/206.23 |
| 4,146,025 | A | * | 3/1979 | Warncke et al. | 128/201.23 |
| 4,253,328 | A | | 3/1981 | Pasternack | |
| 4,294,243 | A | | 10/1981 | Ernsting et al. | |
| 4,296,746 | A | | 10/1981 | Mason, Jr. et al. | |
| RE31,424 | E | | 10/1983 | Ernsting et al. | |
| 4,573,217 | A | | 3/1986 | Reed | |
| 4,589,408 | A | | 5/1986 | Singer | |
| 4,807,614 | A | | 2/1989 | van der Smissen et al. | |
| 4,905,683 | A | | 3/1990 | Cronjaeger | |
| H863 | H | | 1/1991 | Kwiedorowicz et al. | |
| 5,078,130 | A | | 1/1992 | Van Oosten et al. | |
| 5,080,092 | A | * | 1/1992 | Tenna | 128/201.19 |
| 5,181,506 | A | | 1/1993 | Tardiff, Jr. et al. | |
| 5,245,993 | A | | 9/1993 | McGrady et al. | |
| 5,297,544 | A | | 3/1994 | May et al. | |
| 5,575,278 | A | | 11/1996 | Bonhomme et al. | |
| 5,595,174 | A | | 1/1997 | Gwaltney | |
| 5,653,225 | A | * | 8/1997 | Schegerin | 128/201.24 |
| 5,690,095 | A | | 11/1997 | Glynn et al. | |
| 5,816,243 | A | | 10/1998 | Georgiou | |
| 6,161,538 | A | | 12/2000 | Urgei et al. | |
| 6,269,489 | B1 | | 8/2001 | Heath | |
| 6,328,031 | B1 | * | 12/2001 | Tischer et al. | 128/201.25 |
| 6,520,177 | B1 | | 2/2003 | Bonhomme et al. | |
| 2002/0134381 | A1 | * | 9/2002 | Bonhomme et al. | 128/201.24 |

FOREIGN PATENT DOCUMENTS

| | | |
|---|---|---|
| GB | 1315112 | 4/1973 |
| GB | 2080120 | 2/1982 |
| GB | 2179862 | 3/1987 |
| WO | WO 94/19055 | 9/1994 |

OTHER PUBLICATIONS

U.S. Appl. No. 09/572,255, filed May 17, 2000, Bridges.

* cited by examiner

RESPIRATOR ASSEMBLY

The present invention relates to a respirator assembly for the protection of personnel against contaminated or otherwise irrespirable environments. It has particular application for use by aircrew or other military personnel who may be exposed to the risk of nuclear, biological or chemical (NBC) attack, but may be found to be of more general application wherever breathing apparatus must be used, e.g. in firefighting or for industrial use where work must be performed in hazardous environments.

It is recognised that wearing a conventional respirator, which encompasses the whole head or at least the face of the user to isolate the nose, mouth and eyes from the external environment, imposes a considerable physiological burden on the user and severely limits the duration for which it can be worn without reducing the users ability to perform his mission effectively. It is therefore desirable to match the protection to the hazard so that personnel are not required to wear full respirators for extended periods of time when standing by for action or when there may be a threat of a hazard but no actual hazard encountered. On the other hand, donning a conventional respirator, and in particular ensuring that it is adequately sealed against the head to exclude the external environment, can be quite time-consuming, and it may be too late to attempt to don when the hazard is actually encountered. In the case of military combat aircrew who may require NBC protection, for example, it is quite impractical for a conventional, respirator to be donned in flight, meaning in effect that a decision must be made at the commencement of a mission between wearing full protection for the duration of the mission—with the consequent and possibly unnecessary physiological burden which that implies—or no protection.

With the foregoing in mind, respirator assemblies have been proposed which can be worn in a partially disassembled, open face condition to permit free breathing of ambient air, and which are completed with a face piece supplied from a suitable source of breathing gas when the need arises. For example U.S. Pat. No. 5,575,278 discloses an assembly comprising a helmet with a flexible envelope extending downwards and sealing around the neck of the user, and a separate face piece which can be attached to the helmet when required. In this arrangement isolation from the external environment depends on the neck seal which can be uncomfortable to wear and, being a component of the "permanent" part of the respirator, imposes this burden under both the partially disassembled and fully assembled conditions of use. U.S. Pat. No. 5,078,130 discloses an assembly comprising a helmet with a face piece hinged to it which can be tilted up out of the way or pivoted down and pressed back against the helmet to complete the system as required. The face piece carries a seal to seal around the periphery of the user's face when pressed back against the helmet. Isolation from the external environment and conservation of the breathing gas supply depends on the quality of this face seal and in practice it may not be possible to ensure an adequate fit under all likely operational conditions and particularly in haste.

The present invention seeks to provide a respirator assembly which overcomes the above-indicated drawbacks of the prior art and accordingly resides in an assembly comprising: a first sub-assembly adapted to be worn on the head and including sealing means adapted to form a seal around the periphery of the user's face when worn; and a second sub-assembly separable from the first sub-assembly but selectively co-operable therewith, the second sub-assembly comprising a face piece adapted to co-operate with the first sub-assembly to define therewith a facial cavity bounded by said sealing means, inlet means connectable to a source of breathing gas for supply to the user and outlet means for the exhaustion of exhaled gas from the user.

In use of the present invention the first sub-assembly can be donned at the outset and the necessary time taken to ensure that its sealing means is adequately sealed against the user's face before there is any risk of exposure to the hazardous environment for which the respirator is intended. It can be worn in this condition to permit free breathing of ambient air, and with the face seal providing substantially better comfort in use than a constrictive neck seal, until the user is subject to the risk of attack or otherwise required to enter the intended hazardous environment, at which time the second sub-assembly is used to complete the system. An assembly according to the invention may therefore achieve better comfort and/or reliability for the user than those disclosed in U.S. Pat. No. 5,575,278 and U.S. Pat. No. 5,078,130.

The first and second sub-assemblies may be completely separable whereby the first sub-assembly can be worn alone, the second sub-assembly being demountably attachable to the first. Alternatively the second sub-assembly may be hinged or otherwise articulated to the first.

In a preferred embodiment the first sub-assembly comprises headgear including a substantially rigid ring structure adapted to be juxtaposed to the user's face when the headgear is donned and from which said sealing means extend to engage around the periphery of the user's face, the second sub-assembly being configured to be mounted to said ring structure and secured thereto by releasable fastening means. In any event the first sub-assembly may comprise headgear in any appropriate form according to the operational requirements concerned, such as a flexible hood, an impact-resistant helmet, or simply a harness sufficient to hold the rest of the assembly in position.

The respirator assembly may be used with any suitable source of breathing gas in accordance with the intended service. For example it may be connected to a cylinder or other supply of compressed air or oxygen, or a filter canister selected for the hazard in question, with or without fan assistance, all in accordance with conventional practice.

The invention will now be more particularly described, by way of example, with reference to the accompanying drawings in which:—

Figure 2:
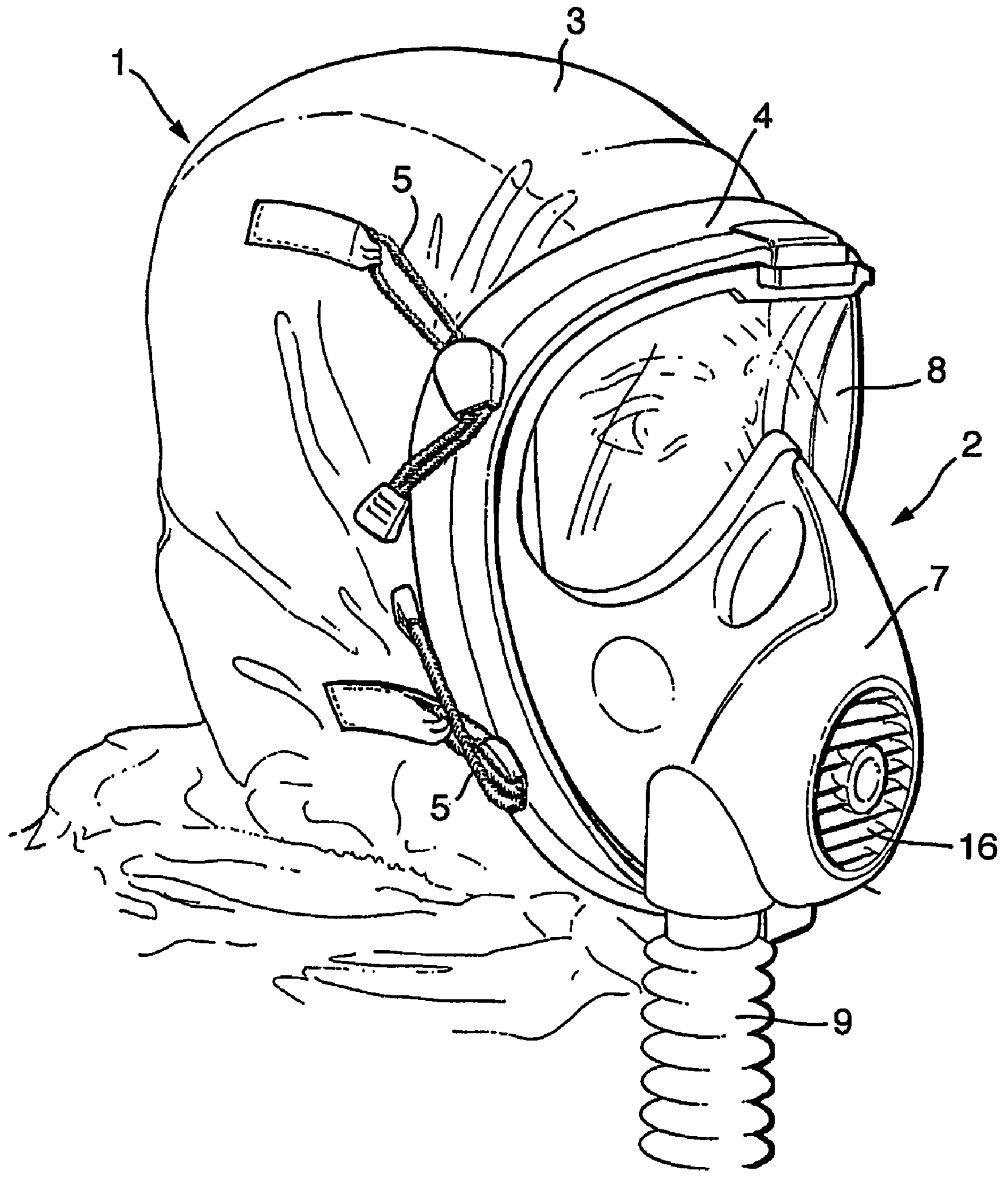
Figure 3:
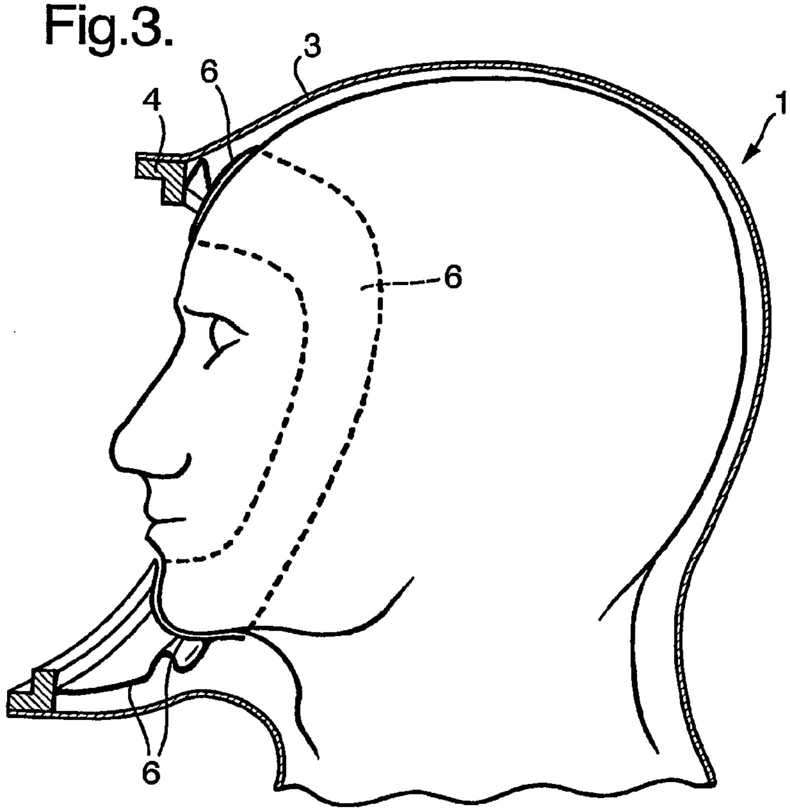
Figure 4:
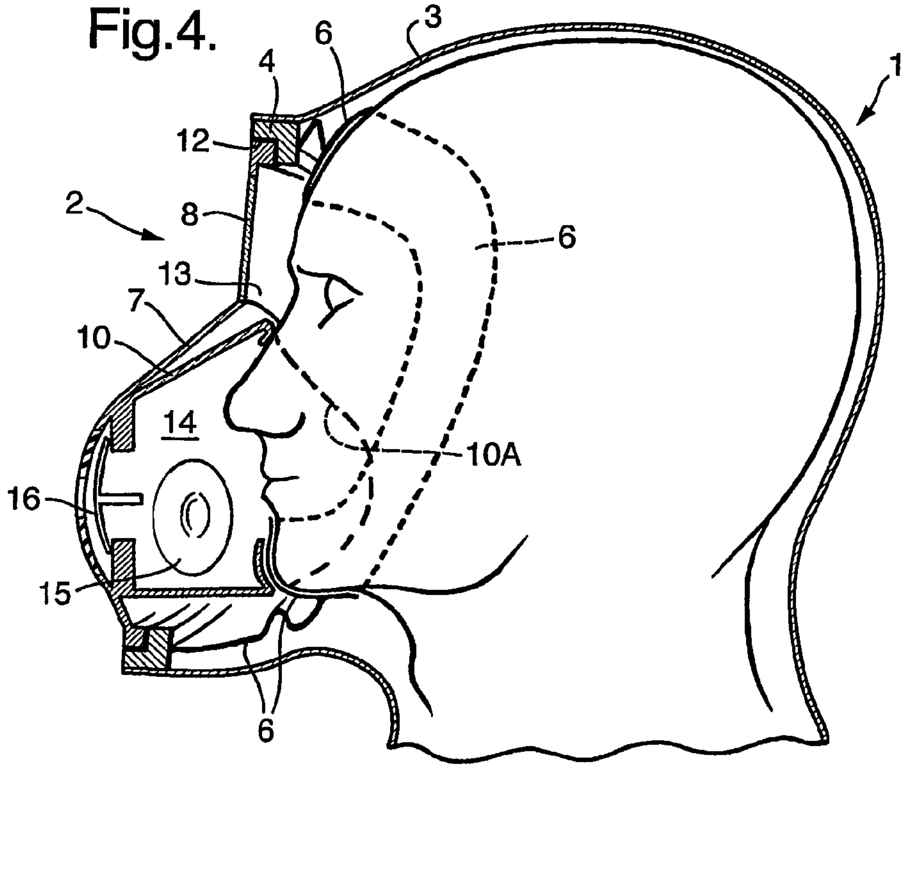

FIGS. 1 and 2 are respective pictorial views of one preferred embodiment of a respirator assembly according to the invention shown in use in its partially disassembled and fully assembled conditions; and FIGS. 3 and 4 are respective schematic cross-sectional views corresponding to FIGS. 1 and 2.

The illustrated embodiment of the invention is in the form of a respirator hood assembly for providing protection against NBC hazards. It comprises a first, hood sub-assembly 1 shown donned on its own in FIGS. 1 and 3 and a second, face piece sub-assembly 2 shown attached to the hood sub-assembly in FIGS. 2 and 4.

With reference to FIGS. 1 and 3, the sub-assembly 1 comprises headgear in the form of a flexible head covering 3 which is also extended downwards over the shoulders of the user, and a substantially rigid profiled ring 4 attached to the head covering so as to encircle the face of the user at an appropriate spacing when the head covering is donned. The ring 4 and covering 3 are secured together around the whole of their mating edges and additional adjustable ties 5 are provided between these elements to assist in supporting the ring 4 and the second sub-assembly 2 when the latter is added. The ring 4 also carries a profiled elastomeric gasket 6 which extends into sealing engagement around the periphery—brow, temples, cheeks and chin—of the user's face when the head covering is donned.

In operation the user can don the sub-assembly 1 as shown in FIGS. 1 and 3, prior to a mission, and take the time to ensure that the gasket 6 is properly and comfortably sealed against his face before there is any risk of exposure to the hazard. He can continue to wear the apparatus in that condition into the mission, breathing ambient air through its open front, until such time (if any) as respiratory protection is required, when the sub-assembly 2 can be added.

With reference to FIGS. 2 and 4, the sub-assembly 2 comprises a moulded face plate 7 with inset lens 8 and a fitted air supply hose 9. Internally it carries an oronasal mask 10 (FIG. 4) with a soft sealing edge 10A to engage around the mouth and nose of the user when donned. The face piece sub-assembly 2 can be demountably attached to the hood sub-assembly 1 and in the illustrated embodiment is retained by lugs (not shown) on the face plate 7 engaging in sockets 11 (FIG. 1) formed on the ring 4, one of which includes a manually-releasable latch 11A. The periphery of the face plate 7 is profiled to match the contour of the ring 4 and carries a seal 12 (FIG. 4) to ensure a gas-tight connection between those elements when attached.

In the fully assembled condition of the respirator shown in FIG. 4 a facial cavity 13 is formed, bounded by the face plate 7 and gasket 6, in which the user's nose, mouth and eyes are isolated from the external environment. The integrity of the peripheral face seal formed by the gasket 6 is crucial in this respect, and can be ensured by the careful donning of the sub-assembly 1 prior to a mission. The sub-assembly 2 can thereafter be donned quickly when required to complete the respirator without compromising the integrity of the face seal. Within the facial cavity 13 a smaller subdivision 14 is formed by the interior of the oronasal mask bounded by the sealing edge 10A, but the integrity of the latter is of secondary importance to the gasket 6.

In use of the respirator air is supplied via the hose 9 (FIG. 2) under a regulated positive pressure and enters the oronasal mask cavity 14 though an inlet 15 fitted with a one-way valve (FIG. 4). Exhaled air is vented to atmosphere through a one-way outlet valve 16. A stream of air is also directed through ports (not shown) in the mask 10 to pass over the interior face of the lens 8 for demisting purposes, in accordance with known practice.

The hood can be worn under an impact-resistant helmet if required and the face piece sub-assembly 2 donned and doffed without removing the helmet. The material of the head covering 3 can be selected to resist inward penetration of hostile airborne droplets and vapours but sufficiently air-permeable to permit evaporative cooling of the user's head, (for example a microporous charcoal-impregnated cloth).

By virtue of the face seal formed by gasket 6 the assembly will be substantially more comfortable to wear, both in the fully assembled and partially disassembled conditions, than those respirator hoods which depend on the provision of a neck seal. The air-permeable head covering 3 will also enhance user comfort. At the same time, by making the gasket 6 part of the sub-assembly 1 which can be donned at leisure, the integrity of the face seal can be more reliably ensured than in those assemblies where a face seal is applied only when a threat is encountered and likely in haste.

In a variant of the illustrated embodiment the lens 8 is provided in a separate unit which can be sealingly attached to the face plate 7 or removed from it if required. The remainder of the assembly can therefore be worn without the lens unit to partially relieve the physiological burden on the user when there is no threat of contamination but e.g. when aircrew require to wear the mask 10 for hypoxia and/or G protection, the lens unit subsequently being added if a threat is encountered.

The invention claimed is:

1. A respirator assembly comprising: a first sub-assembly adapted to be worn on the head and including a gasket adapted to seal against the periphery of the user's face when worn; and a second sub-assembly separable from the first sub-assembly but selectively co-operable therewith, the second sub-assembly comprising a face piece adapted to co-operate with the first sub-assembly to define therewith a facial cavity bounded by said gasket, an inlet connectable to a source of breathing gas for supply to the user and an outlet for the exhaustion of exhaled gas from the user.

2. A respirator assembly according to claim 1 wherein the first and second sub-assemblies are completely separable whereby the first sub-assembly can be worn alone, the second sub-assembly being demountably attachable to the first sub-assembly.

3. A respirator assembly according to claim 2 wherein the first sub-assembly comprises headgear including a substantially rigid ring structure adapted to be juxtaposed to the user's face when the headgear is donned and from which said gasket extends to engage around the periphery of the user's face, the second sub-assembly being configured to be mounted to said ring structure and secured thereto by at least one releasable fastener.

4. A respirator assembly according to claim 1 wherein the second sub-assembly is articulated to the first sub-assembly.

5. A respirator assembly according to claim 1 wherein the first sub-assembly comprises headgear in the form of a flexible hood of air-permeable material.

6. A respirator assembly according to claim 1 wherein the second sub-assembly includes an oronasal mask to be disposed within said facial cavity.

7. A respirator assembly according to claim 1 wherein said face piece includes a demountable lens portion.

* * * * *